United States Patent [19]
Dietzel

[11] Patent Number: 5,166,526
[45] Date of Patent: Nov. 24, 1992

[54] APPARATUS AND METHOD FOR MEASURING THE RADIOACTIVITY OF AN ELUATE

[75] Inventor: Günter Dietzel, Straubenhardt, Fed. Rep. of Germany

[73] Assignee: Raytest, Isotopenmessgeräte GmbH, Straubenhardt, Fed. Rep. of Germany

[21] Appl. No.: 707,580

[22] Filed: May 30, 1991

[30] Foreign Application Priority Data

Jun. 1, 1990 [DE] Fed. Rep. of Germany ....... 4017810

[51] Int. Cl.⁵ ............................................. G01T 1/167
[52] U.S. Cl. ................................ 250/430; 250/432 R; 250/435
[58] Field of Search ................. 250/432 R, 435, 364, 250/328, 430

[56] References Cited

U.S. PATENT DOCUMENTS 4,194,117 3/1980 Gross .................................. 250/328
4,704,531 11/1987 Berthold et al. .................... 250/364

FOREIGN PATENT DOCUMENTS 3233187 3/1983 Fed. Rep. of Germany .
3329133 2/1985 Fed. Rep. of Germany .
105075 6/1983 Japan .............................. 250/432 R
44677 3/1984 Japan .............................. 250/432 R

OTHER PUBLICATIONS

"Radio-Flüssigkeitssaulen-Chromatographic", K. Figge et al. G-I-T Fachz. Lab 19 Jg, Mar. 1975, pp. 192-202.

Primary Examiner—Carolyn E. Fields
Attorney, Agent, or Firm—Anderson Kill Olick & Oshinsky

[57] ABSTRACT

An arrangement for measuring radioactivity of an eluate flow with a flow-through detector arrangement, including at least one radioactivity detector, and a valve arrangement by way of which the eluate flow can be redirected through the at least one radioactivity detector where the radioactivity of the eluate is measurable in a stationary manner.

10 Claims, 2 Drawing Sheets

APPARATUS AND METHOD FOR MEASURING THE RADIOACTIVITY OF AN ELUATE

BACKGROUND OF THE INVENTION

The invention is directed to an apparatus and a method for measuring the radioactivity of an eluate by a flow-through detector arrangement.

It is known in radiochromatography to measure the radioactivity of the liquid eluate (eluation agent) carrying the radioactive fraction by means of a flow-through detector, through which eluate flows.

The measurement of the radioactive radiation is herein subject to the statistical fluctuation of the emission of the radiation particles. The statistical error caused hereby corresponds to the square root of the quantity of the measured events (Sigma=$\sqrt{n}$, wherein Sigma designates the statistical error and n the total quantity of the measured events). 95.5% of all measured values lie within the limits of $\pm 2$ Sigma, which values can be acquired with an average value of n.

When measuring radioactivity in a flow-through detector, n events per second are registered. If one multiplies this number by the dwelling time of the radioactively marked fraction in the flow-through measuring cell, then one gets the total number of the events acquired during the flow-through process. The dwelling time in the measuring cell of the radioactively marked fractions flowing through the measuring cell is computed from the quotient of measuring cell volume divided by the flow velocity.

In order to reduce the statistical measuring error, it could be considered to lengthen the measuring cell so that the transit period is correspondingly increased and the quantity of the measured events is increased. For instance, if the measuring cell were twice as large, the transit period would be doubled and with this also the quantity of the measured events would become twice as large, so that the specific error Sigma ($\sqrt{n}$) would be correspondingly reduced. Such an increase in the size of the measuring cell leads however to a corresponding increased fabrication cost and also reduces the resolution ability of the measuring cell, since radioactive fractions following rapidly upon each other can no longer be measured selectively, since the previous radioactive fraction can still be in the measuring cell while the subsequent radioactive fraction is already flowing into the same measuring cell. The measuring result is then composed of the radiation results of both radioactive fractions together, so that it is no longer possible to discriminate clearly or no longer possible to discriminate at all between the radioactive fractions and their associated radioactive peaks.

On the other hand a detection sensitivity in measuring cells with the usual volume size is not very high, since due to the relatively high error fluctuation width, a very weak radioactivity rate cannot be reliably differentiated from the zero effect rate and its statistical fluctuation. This entails that the detection sensitivity limit, above which the presence of a radioactive fraction can even begin to be reliably registered, is relatively high.

SUMMARY OF THE INVENTION

Accordingly, it is an object of the present invention to provide an apparatus and a method for continuous measurement of the radioactivity of an eluate, which permits a comparatively precise measurement of the radioactivity at a high detection sensitivity.

Pursuant to this object, and others which will become apparent hereafter, one aspect of the present invention resides in an arrangement for measuring radioactivity of an eluate flow by means of a flow-through detector arrangement, including at least one radioactivity detector and a valve arrangement for redirecting the eluate flow from a normal flow path through at least one radioactivity detector where the radioactivity of the eluate can be measured in a stationary manner. Thus, in the invention, the eluate to be measured can be conducted through at least two different flow paths, wherein a radioactivity detector is present in at least one of these flow paths, with the eluate remaining for a specific interval stationary therein so as to be measured in this radioactivity detector. This stationary measurement of the radioactivity leads to the dwell time of the eluate in the radioactivity detector and consequently the measuring period can be considerably lengthened. Hereby there results that a pronounced diminution of the statistical error, meaning of the relative fluctuation width. If, for instance, the counting rate is 1 per second and the dwell time in the radioactivity detector is approximately 20 seconds, the statistical fluctuation width amounts to Sigma 22.3%. Compared to this, the statistical fluctuation width Sigma, with the same counting rate but with the dwell time being only half as large amounting to 10 seconds, would be 31.6%, meaning still considerably more. The error width thus is significantly reduced by the increase of the inventive measuring duration. At the same time the detection sensitivity increases in a pronounced manner, because even weak radioactive fractions can be clearly discriminated from interferences, meaning zero effects, because of the overall higher counting results.

If the points in time when the expected radioactive fractions flow through the normal flow path are known, then a single radioactivity detector suffices in the simplest case, wherein the valve arrangement then can be chronologically controlled way in a targeted manner so that the expected radioactive fractions are consecutively and selectively diverted from the normal flow path to the radioactivity detectors and are there measured in a stationary manner. The measuring duration is then determined by the time interval until the subsequent radioactivity fraction appears. The normal flow path can in this case discharge for instance into a waste container.

The measuring apparatus and the measuring method can however be extensively automated if a monitor detector is provided upsteam of the valve arrangement, which registers the activity peaks and issues a control signal for changeover of the valve arrangement when they occur. The control signal can still be applied directly to the valve arrangement by the monitor detector. Preferably, however, the control signal is indeed supplied to a control arrangement, or at least to a delay arrangement, which is laid out so that the valve arrangement is changed over in a targeted manner to at least one radioactivity detector at that point in time, when the radioactivity fraction arrives at the valve arrangement.

The monitor detector cannot only be used for registration of the activity peak, rather in a refinement of the invention it can at the same time also perform quantitative evaluation of the radioactivities of the individual radioactivity fractions. In this case it is possible to feed only then a changeover signal to the valve arrangement for redirection of the eluate to at least one radioactivity detector, if for instance it is not clear in the range of the detection limit of the monitor detector with very weak counting results, whether one deals in fact with a weak radioactivity fraction or with malfunctions. In this case it can be reliably recognized in at least one radioactivity detector because of stationary evaluation of this weak active eluate share, whether we are effectively dealing with a radioactivity fraction and how strong this fraction is or whether merely malfunction effects are present. The radioactivity detectors in this case thus serve as an additional counting segment, which is only activated when selectively heightened measuring accuracy are required. The at least one radioactivity detector, not in this case, thus measures in a stationary manner the entirety of radioactivity fraction, rather does not evaluate merely individual selectively fed fractions.

According to a further embodiment, the valve arrangement is again switched back to the normal flow path at the end of the registered activity peak, so that only the detected radioactive fraction is stored and measured in the radioactivity detector, without running the danger of its dilution or partial flushout by eluate free of radioactivity which is subsequently flowing in. Because of this concentrated measurement, a very high measuring accuracy can be achieved also with fractions having only weak radioactivity.

The valve arrangement can, for instance, be designed in such a way that the normal flow path (downstream of the monitor detector, if such is present) subdivides into at least two branches, of which one is a normal flow path and the other, or the others, lead to one or several radioactivity detectors, and individually controllable valves exist in all of these divided branches, which are opened or closed to correspond with the desired eluate flow.

Preferably, the valve arrangement is constructed as a changeover valve with at least two outlets, by means of which the eluate flow can be redirected selectively either to continue along the normal flow path or be directed to one or, if they exist, several radioactivity detectors. This design has a simple and rugged structure and can also be controlled simply and reliably.

In addition, the embodiment with a central changeover valve is also less prone to malfunction and in case of necessity easier to repair than the system with several decentralized valves.

According to a further embodiment, the normal flow path discharges into a waste container. This has the advantage that the eluate can continuously flow into this waste container, as long as no radioactive fraction has been identified. The eluate shares free of radioactivity are thus collected in a targeted manner and can be easily disposed of. Due to the switchover of the radioactive fractions to at least one radioactivity detector, it is simultaneously achieved that these radioactive eluate shares are extracted from the normal flow path and therefore do not reach the waste container, so that the eluate collected in this waste container does not contain any radioactive shares. This is an advantage for simple disposal.

In yet another embodiment, the outlet of at least one radioactivity detector is connected with a collection device for fractions, so that the measured radioactive fractions can then be collected in a targeted manner, preferably separately.

In still another embodiment, two radioactivity detectors in parallel are provided which are coupled on an inlet side with separate outlets of the valve arrangement, and on the outlet side are coupled with a fraction collector. This construction enables a radiochromatography evaluation with very high measuring precision and high sensitivity, wherein the design effort expended is in spite of that relatively low.

Especially if switchover occurs cyclically between the two radioactivity detectors in the case of each occurring activity peak, every radioactive fraction can be measured in a stationary manner in the radioactivity detector up to the appearance of the respective one after the next activity peak, so, that as a rule, a very long measuring interval with correspondingly high measuring accuracy and detection sensitivity is achieved.

In another embodiment, a flushing device is provided by which a very thorough and rapid flushing of the one or several radioactivity detectors can be achieved after termination of a measuring process and prior to the renewed filling of the respective radioactivity detector with a new radioactive fraction, so that the radioactivity detector is preferably completely or at least largely devoid of residual radioactivity and the subsequent measuring process is thus not adulterated by radioactive residues of the previous measuring cycle.

Due to the valve-controlled flushing of still another embodiment which has a driven flushing pump, a storage container for the flushing agent, and a flush valve which has an outlet connected with the radioactivity detectors, only one single flushing arrangement is required for all radioactivity detectors, all of which can be selectively flushed by means of the appropriate valve position which minimizes the design and the construction expenditure.

A method is also disclosed which arrives at the same results as the apparatus discussed above, and is the basis on which the apparatus operates.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF THE PREFERRED EMBODIMENTS

Figure 1:
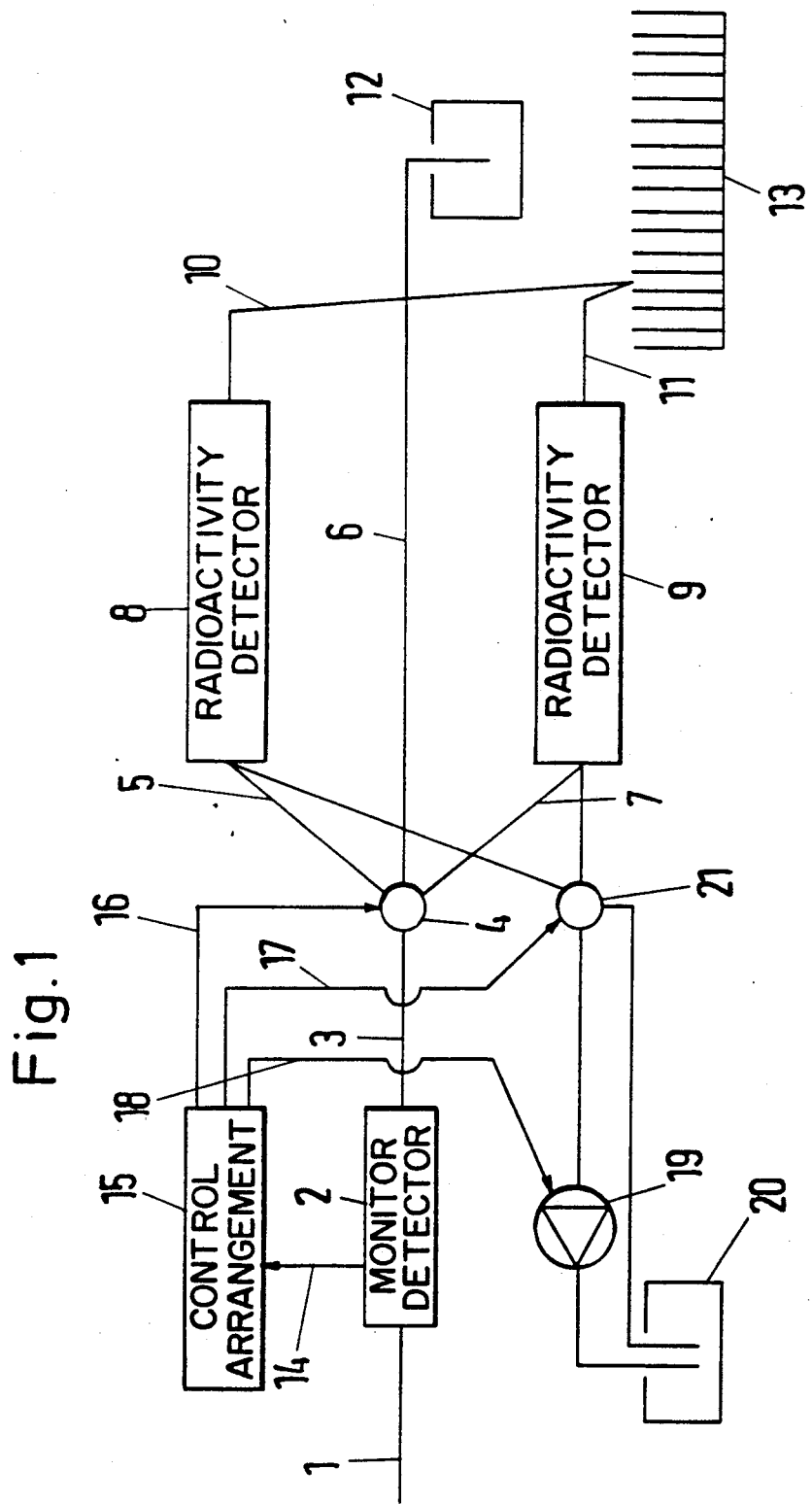
FIG. 1 shows an embodiment of the measuring arrangement pursuant to the present invention.

In the embodiment of the measuring arrangement shown in FIG. 1, the eluate carrying the radiochromatogram is directed through an inlet line 1 to a monitor detector 2 which monitors the occurrence of radioactivity peaks and possibly additionally performs a quantitative measurement of the radioactivity. The monitor detector 2 is configured as a flow-through detector. The eluate is fed from the monitor detector 2 through a line 3 to a valve 4, which comprises a fluid inlet connected to the line 3 as well as three fluid outlets, which are in connection with the lines 5, 6 and 7. The valve 4 forms a valve arrangement and is configured as a reversal or changeover valve, which respectively connects the inlet only with one of the three outlets, so that one can respectively switch between the outlets, depending upon a control signal supplied through a single line 16 by a control arrangement 15.

Line 5 leads from the valve 4 to a radioactivity detector 8, which can be configured as a flow-through detector just like the monitor detector 2 and can be connected through a line 10 on its outlet side with a fraction collector 13. Line 6 leads from the valve 4 to a waste container 12 without the interposition of a detector. Line 7 leads from the valve 4 to a second radioactivity detector 9, which can also be laid out as a flow-through detector and is connected with the fraction collector 13 by a line 11 on its outlet side.

When registering an activity peak in the eluate, the monitor detector 2 produces a control signal which is directed through a signal line to the control arrangements 15. As a function of such a detection signal on the signal line 14 the control arrangement 15 generates a switchover signal, which is applied to the valve 4 through the signal line 16. In the normal case, meaning if the monitor detector 2 registers no radioactivity, the outlet of valve 4 is switched to the line 6, so that a non-radioactive eluate continuously flows into the waste container 12. If a switchover signal appears on the signal line, the outlet of valve 4 is switched to line 5 or to line 7. This changeover occurs preferably alternately, so that the valve, if if has been switched to line 5 at the last control signal, is redirected to line 7 at the appearance of the subsequent control signal and at the following control signal is again switched to line 5, etc. This reswitching control can be realized either by the circumstances that the changeover signal on the signal line 16 can assume two different signal states in addition to its state of rest or neutral state, wherein each signal is assigned respectively to one switchover position of the valve, or by the control signal having only one signal state, however with the valve 4 being reswitched automatically and alternately to either lines 5 or 7 at each appearance of a control signal.

The switchover of valve 4 to one of the two lines 5 or 7 can occur directly by means of the monitor detector 2 when an activity peak is registered. In that case the flow through the activated radioactivity detector starts immediately. This has the disadvantage that a possibly just-measured radioactivity fraction in the activated radioactivity detector is immediately flushed out, so that the measuring period is reduced. In addition, the radioactivity detector is then to begin with still flushed through by radioactivity-free eluate, which then, after outlet from the radioactivity detector, would have to be collected in its own waste container, for instance, the fraction collector 13.

Therefore, the valve 4, when it registers an activity peak, is preferably activated with such a time control or time delay, that the valve changeover occurs only when the radioactivity fraction triggering the registered activity peak has just arrived at the valve 4.

The switchback of valve 4 onto the line 6 can occur after a fixed predetermined time interval, which corresponds to the average or maximum width of one activity peak. Preferably, however, the end of the just registered activity peak is also determined and the valve 4 is reswitched to line 6 defining the normal flow path (or with directly following second activity peak onto the other radioactivity detector), this after a time interval corresponding to the measured width of the activity peak. Valve 4 is consequently for a short time switched over to the filling of one of the two radioactivity detectors 8, 9 for introduction of the radioactive fraction into this radioactivity detector after the appearance of a radioactive fraction, then the valve is again switched back to the normal flow path, meaning to the line 6. In the activated or triggered radioactivity detector the radioactive fraction is then measured for such a length of time in the stationary state, until the one after the next activity peak appears. The measuring interval is thus very long, so that the measurement results are correspondingly accurate and the detection sensitivity is high.

A flushing device is provided in order to further improve the measurement accuracy and sensitivity, which flushing device comprises a flushing pump 19, a storage container 20 for flushing liquid and a flushing valve 21. The radioactivity detectors 8 and 9 can be intensively and selectively flushed for a short time immediately after a radioactivity measuring process by means of the flushing device, before introducing a new radioactive fraction into the respective radioactivity detector for performing a new measuring process. Because of the flushing of the radioactivity detector involved, all the radioactive shares remaining from the previous measurement specimen can be preferably completely or at least largely removed, so that the subsequent measuring process of the new radioactive fraction is not influenced or impaired by the previous radioactive fraction. Because of this selective measurement of each radioactive eluate share without any sort of influence through radioactive contaminations remaining from previous measuring processes, it is thus possible to obtain reliable, affirmative measuring results with very high detection sensitivity.

The control of the flushing device can be achieved by a separate control unit. Preferably the control of the flushing device is however also assumed by the control arrangement 15, and actually in such a way that when a new activity peak is registered by means of the monitor detector 2 prior to the switchover of the valve 4, to begin with, electrical signals are applied to the flushing valve 21 and the flushing pump 19 through the signal lines 17 and 18, which cause the flushing valve 21, which can be switched to several passage possibilities, to be set to passage from the flushing pump 19 to the radioactivity detector 8 or 9 which is to be newly fitted and the flushing pump 19 to be switched on. The radioactive fraction still present in the newly to be filled radioactivity detector 8 or 9 is then to begin with flushed into the fraction collector 13 or another recovery container, wherein this flushing process can be performed by the flushing agent or the eluation agent. After that, a short intensive flushing of the newly to be filled radioactivity detector can be performed, wherein the flushing agent is drained after the flushing process into a waste container or also, preferably after purification, can be returned into the flushing agent storage container 20.

After the flushing process the flush valve is switched over in such a way that the flushing agent no longer flows into the newly to be filled radioactivity detector, which subsequently is to be filled by the radioactive fraction to be measured through the appropriate setting of the valve 4. The flush valve 21 can, after termination of the flushing process, be either moved into a complete blocking position or repositioned so that the flushing agent conveyed by the flush pump 19 is again directed into the storage container 20. This has the advantage of keeping the flushing pump 19 continuously in operation during the entire measuring cycle, so that no interval for coming up to speed (required when switching the flushing pump on) arises until an adequate flushing effect is obtained. In this case, meaning with continuously operating flushing pump 19, the signal line 18 can be eliminated.

Figure 2:
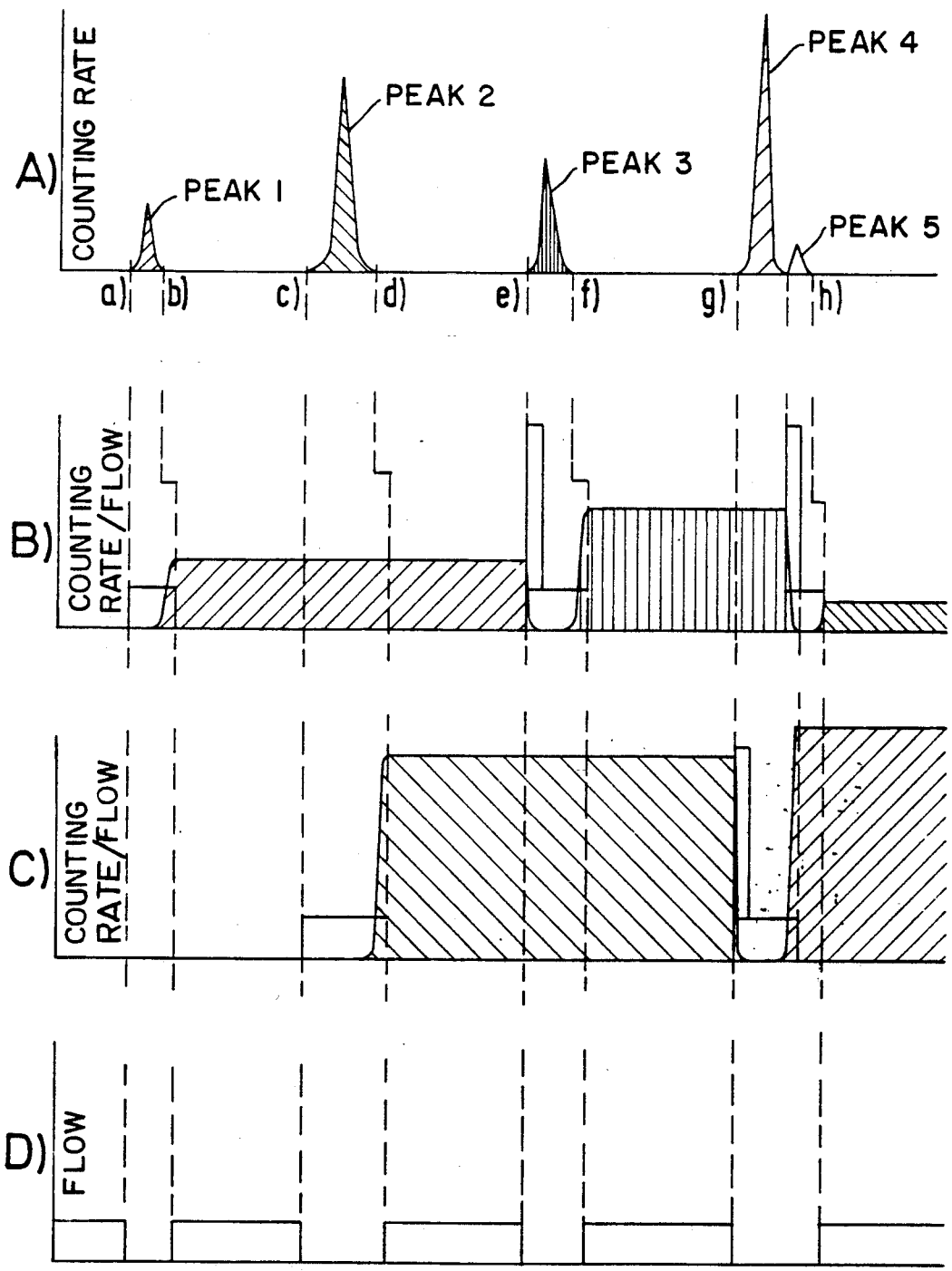
FIG. 2 shows the interconnections between the occurrence of activity peaks and the eluate flow control as well as the detector measuring processes.

In that case the flushing valve 21 has three outlets, of which one is connected with a radioactivity detector 8, the second with a radioactivity detector 9 and the third with a storage container 20, while the inlet of the flushing valve 21 is coupled with the flushing pump 19. The chronological relationship between the occurrence of activity peaks and the filling-, flushing- and measuring processes of the radioactivity detectors 8 and 9 is shown in detail in FIg. 2.

In FIG. 2A five activity peaks are shown on the axis indicating time (abscissa), which occur at irregular time intervals. The amplitude of the activity peaks demonstrates the magnitude of the associated radioactivity.

FIGS. 2B and 2C show the wide, flat unshaded rectangles representing the filling process, the shaded regions representing the measuring intervals and the narrow high rectangles representing the flushing interval, and actually respectively for the radioactivity detector 8 (FIG. 2B) and for the radioactivity detector 9 (FIG. 2C).

The flow sequence of the normal flow path that is in line 6 to the waste container 12 is depicted in FIG. 2D.

At the start of the radioactivity measurement of the eluate, the valve 4 is positioned so that the eluate flows into the waste container 12 through the line 6. This valve position is maintained until the first activity peak appears in the chromatogram. When the first scanning peak 1 of a duration from time point a) to time point b) is registered, the valve 4 is switched so that the eluate flow is directed to the radioactivity detector 8 and the radioactive fraction is stored therein. A short time after the end of the scanning peak 1 (time point b)) has been determined, the valve 4 switches the eluate flow again in the direction of the waste container 12. The radioactivity of the activity peak 1 is now stationarily measured in the radioactivity detector 8, and namely up to the appearance of the activity peak 3 after the next peak 2, which starts at time point e). This measuring process is shown shaded.

As soon as the second activity peak 2 appears (time point c)), the valve 4 switches onto the second radioactivity detector 9, so that this detector is filled with the radioactive fraction causing activity peak 2. Shortly after the termination (time point d) of the activity peak 2, valve 4 switches again to line 6 and thus to the waste container 12 so that the radioactivity with the activity peak 2 is measured in a stationary manner in the radioactivity detector 9, and namely, up to time point g), at which time the activity peak 4 after the next peak 3 starts.

When the third activity peak 3 occurs at the time point e), the flush valve 21 is switched into the direction of the radioactivity detector 8 which is flushed for a short time period at a high flow rate. The flushing time is of such a duration as the base point of the arriving activity peak requires in order to enter the radioactivity detector 8 or 9. After the short intensive flushing process the eluate flows at a preset flow rate into the radioactivity detector 8. As soon as the radioactivity detector is filled with the activity peak 3 lasting up to the time point f), valve 4 switches to line 6 and thus back to the waste container 12. The radioactivity of the activity peak 3 is now measured in a stationary manner in radioactivity detector 8.

At the start of activity peak 4 at the time point g) radioactivity detector 9 is subjected to a short period of intensive flushing in the way as described for radioactivity detector 8 and then the eluate with activity peak 4 is filled into the radioactivity detector 9. Shortly after the termination of the activity peak 4 at time point h), the filling process of radioactivity detector 9 is interrupted, so that activity peak 4 can now be measured stationarily in radioactivity detector 9.

At the same time, the monitor detector 2 determines that activity peak 5 is already following. Therefore, radioactivity detector 8 is now subjected to an intensive flushing process, in order to flush the radioactive fraction of activity peak 3 out of radioactivity detector 8. Directly afterwards the radioactivity detector is filled with the eluate corresponding to activity peak 5. At the end or shortly after the end (time point e)) of activity peak 5, valve 4 is again switched into the direction of line 6 to the waste container 13. Thus, the eluate with activity peak 4 is now located in radioactivity detector 9 for the purpose of stationary measurement and the eluate with activity peak 5 is located in radioactivity detector 8 for stationary measurement.

The above-mentioned processes are repeated with the occurrence of additional activity peaks.

If only one of the radioactivity detectors 8 or 9 is used, meaning the other radioactivity detector is absent to begin with or is not activated, then the radioactive fraction can be measured in a stationary manner in the radioactivity detector until the new activity peak arrives. In the case of two stationary radioactivity detectors as described in the embodiment above, the radioactivity fraction can be stationarily measured in one of the radioactivity detectors until the one after the next activity peak arrives. If n stationary radioactivity detectors are used, the first activity peak can be stationarily measured by the first radioactivity detector until the activity peak n+1 appears.

The sensitivity improvement, which can be achieved with the arrangement and the process in the invention, corresponds to the square root of the quotient (dwelling time in the stationary radioactivity detector/normal transit time through the monitor detector). If the dwell time is for instance of 100s duration and if the normal transit time corresponds to 10s, then there results a sensitivity improvement by the factor of 3.16.

In the embodiment described there exist two radioactivity detectors 8 and 9. It is however also possible to utilize only one single radioactivity detector for the stationary measurement. This reduces also the number of the required outlets of the valves 4 and 21. Such an arrangement is adequate for many applications. In radiochromatrography it occurs quite frequently that only one activity peak appears in the entire chromatogram. This activity peak can be measured in the radioactivity detector in a stationary manner beginning with the point in time of its appearance until the termination of the chromatogram.

Alternatively, it is also possible not to direct every activity peak into the stationary radioactivity detector, rather only selected radioactive fractions, for instance such where the amplitude of the output signal generated by the monitor detector 2 is so small, that one is obliged to investigate more closely in a stationary manner, whether one is dealing herein with effective radioactive fractions or only with disturbances.

The embodiment described with two radioactivity detectors 8, 9 in parallel is optimal for the case which is not rare, when two activity peaks appear in the chromatogram, which can then be respectively measured in a stationary manner from the instant of their appearance up to the termination of the chromatogram. However, also in case of several activity peaks there results a considerable lengthening of the measuring time in the embodiment described, so that a considerably larger quantity of pulses is collected. This leads to a considerably smaller relative statistical fluctuation, so that the radioactivity counting rate can be determined with considerably higher accuracy.

Naturally, the embodiment can also be modified in such a way that three or more radioactivity detectors are connected to the appropriate outlets of valve 4 and cyclical switching is done between the radioactivity detector at the appearance of respective activity peaks. This permits lengthening the dwell time of the eluate share corresponding to the activity peaks in the appropriate radioactivity detectors, so that the accuracy and the detection sensitivity are accordingly increased.

In a refinement of the invention, it is furthermore possible to eliminate the fraction collector 13, wherein the outlets of the radioactivity detectors 8 and 9 are then connected either to the waste container 12 or to a waste container of their own.

It is equally also possible to eliminate the monitor detector 2, if the time grid of the appearance of the activity peaks is already known or is registered by another component. The valve 4 is then controlled to correspond with this time grid.

Furthermore, the control signal generated by the monitor detector 2 can be directly sent to the valve 4 and to the flushing valve 21, wherein then preferably appropriate time delay links are contained in the control lines between the monitor detector 2 and the valves 4 and 21. In this case the control arrangement 15 can also be eliminated.

The lines containing the eluate and the flushing agent can be formed by tubes or hoses or also in another way.

Futhermore, it is possible to eliminate the flushing device 19, 20, 21. In that case, the valve 4 is preferably switched timewise early at the appearance of a new activity peak, so that the radioactivity detector selected can still be adequately flushed by the eluate, until the new radioactivity fraction corresponding to the activity peak is introduced into the radioactivity detector involved.

If the flushing device is present as described previously, then no flushing process must be performed at least prior to the first filling process of that stationary radioactivity detector or detectors. This is also discernible from FIG. 2.

The arrangement in the invention and the process in the invention thus make it possible to maintain a continuous eluate flow preferably also at a constant rate and in spite of that to measure selected eluate shares in a stationary way, whereby high measuring accuracy and high detection sensitivities are achieved with a comparatively simple construction.

While the invention has been illustrated and described as embodiment in an apparatus and method for measuring the radioactivity of an eluate, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters patent is set forth in the appended claims.

1. An arrangement for measuring radioactivity of an eluate flow with a flow-through detector arrangement, comprising:
   at least one radioactivity detector;
   valve means for redirecting the eluate flow from a normal flow path through the at least one radioactivity detector where the radioactivity of the eluate is measurable in a stationary manner; and
   monitor detector means arranged upstream of the valve means for reqistering activity peaks and generating a control signal when activity peaks occur, the valve means being switched over to introduce the eluate into the at least one radioactivity detector in dependence upon the control signal, and switched back to the normal flow path at or after the end of a registered activity peak, said normal flow path discharging into a waste container.

2. An arrangement according to claim 1, wherein the valve means is a changeover valve with at least two outlets.

3. An arrangement according to claim 1, and further comprising a fraction collector connected to an outlet of the at least one radioactivity detector, so that measured radioactive fractions are collectable therein together or separately.

4. An arrangement according to claim 1, wherein two radioactivity detectors in parallel are provided, which are coupled on an inlet side with separate outlets of the valve means and on an outlet side with a fraction collector.

5. An arrangement according to claim 4, wherein the valve means is arranged so as to alternatively introduce consecutive radioactive fractions into the two radioactivity detectors.

6. An arrangement according to claim 1, and further comprising flushing means for flushing the at least one radioactivity detector upon termination of one radioactivity measurement and prior to introduction of a new radioactive fraction.

7. An arrangement according to claim 6, wherein the flushing means includes an at least intermittently driven flushing pump, a storage container for a flushing agent and a flush valve which has an outlet connected through a line with the at least one radioactivity detector.

8. A method for measuring the radioactivity of an eluate flow by means of a flow-through detector arrangement, comprising the steps of:
   registering activity peaks of the eluate flow by means of a monitor detector means;
   directing a portion of the radioactive eluate into a radioactivity detector;
   then switching off the eluate flow by the radioactivity detector in order to measure the radioactivity thereof in a stationary manner; and
   removing the measured eluate flow portion from the radioactivity detector, non-radioactive eluate flow portions being directed into a waste container while bypassing the radioactivity detector.

9. A method according to claim 8, including removing an eluate flow portion present in the radioactivity detector from the radioactivity detector at an appearance of a new radioactive fraction in the eluate following at a later point in time, introducing the new radioactive fraction into the radioactivity detector and then again switching off the eluate flow by said radioactivity detector.

10. A method according to claim 8, including flushing out the radioactivity detector prior to introduction of a following radioactive fraction.

* * * * *